United States Patent [19]

Pavilon

[11] Patent Number: 4,952,504
[45] Date of Patent: Aug. 28, 1990

[54] METHOD FOR PRODUCING ETHANOL FROM BIOMASS

[76] Inventor: Stanley J. Pavilon, 18519 Lomond Blvd., Shaker Heights, Ohio 44122

[21] Appl. No.: 79,138

[22] Filed: Jul. 28, 1987

[51] Int. Cl.⁵ .............................................. C12P 7/10
[52] U.S. Cl. ...................................... 435/163; 426/49; 426/52; 426/53; 426/54; 426/616; 426/635; 426/807; 435/164; 435/165
[58] Field of Search ........................ 435/163, 164, 165; 426/49, 52-53, 54, 616, 635, 807

[56] References Cited

U.S. PATENT DOCUMENTS

| | | | |
|---|---|---|---|
| 930,274 | 8/1909 | Doughty . | |
| 1,323,540 | 12/1919 | Moore . | |
| 1,888,935 | 11/1932 | Placek . | |
| 2,561,072 | 7/1951 | Reich ................................. | 195/33 |
| 2,686,146 | 8/1954 | Buswell et al. ..................... | 195/13 |
| 4,009,075 | 2/1978 | Hoge ................................... | 195/33 |
| 4,242,455 | 12/1980 | Muller et al. ...................... | 435/162 |
| 4,287,303 | 9/1983 | Dahlberg et al. .................. | 435/162 |
| 4,321,328 | 3/1982 | Hoge ................................... | 435/165 |
| 4,334,026 | 6/1982 | Chynoweth et al. ............... | 435/163 |
| 4,355,108 | 10/1982 | Gaddy et al. ....................... | 435/165 |
| 4,421,856 | 12/1983 | Muller et al. ...................... | 435/161 |
| 4,425,433 | 1/1984 | Neves ................................. | 435/163 |
| 4,436,586 | 3/1984 | Elmore ............................... | 162/19 |
| 4,461,648 | 7/1984 | Foody .................................. | 127/37 |
| 4,497,896 | 2/1985 | Assarsson et al. ................. | 435/161 |
| 4,503,079 | 3/1985 | King et al. .......................... | 426/54 |
| 4,517,298 | 5/1985 | Tedder ................................ | 435/160 |
| 4,529,699 | 7/1985 | Gerez et al. ........................ | 435/165 |
| 4,547,226 | 10/1985 | Milch et al. ........................ | 127/41 |
| 4,564,595 | 1/1986 | Neves ................................. | 435/163 |

OTHER PUBLICATIONS

Weinberg et al., "The Effect of Sorbic Acid on Loss Reduction During Storage of Orange Peels", J. Sci. Food Agric, 46 (3), pp. 255–258, 1989.

Weinberg et al., "The Effect of Treatment with Urea Sorbic Acid or Dehydration on Orange Peel Silage", Anim Feed Sci. Techol, 20 (4), pp. 335–342, 1988.

Ashbell et al., "Dynamics of Orange Peel Fermentation During Ensilage", J. Appl. Bacterol, 63 (4), pp. 275–280, 1987.

Hara et al., J. Jpn. Soc. Food Sci. Technol. 32 (4), pp. 241–246, 1985.

Ward Worthy, "Cellulose-to-Ethanol Projects Losing Momentum", Dec. 7, 1981, pp. 35–42, C&EN.

Primary Examiner—Robert J. Warden
Assistant Examiner—Timothy M. McMahon
Attorney, Agent, or Firm—Jones, Day, Reavis & Pogue

[57] ABSTRACT

Biomass slurry is hydrolyzed in a fuel fired hydrolysis heater. When the biomass is fruit waste, the organic acid in the waste is used as the hydrolysis catalyst. When the biomass does not contain organic acid, carbon dioxide generated in a fermenter is fed to the hydrolysis heater as carbonic acid to provide the catalyst. Solids are separated from the hydrolyzed effluent, and flue gas from the hydrolysis heater is used to dry same. The effluent is fermented and subsequently distilled at substantially atmospheric pressure to produce ethyl alcohol vapor. The vapor is fed to a vacuum distillation tower for producing anhydrous ethyl alcohol. Vacuum distillation tower bottoms provide the reflux for the atmospheric distillation unit. A portion of the stillage from the atmospheric distillation unit is recycled by mixing with new feedstock. The remaining stillage is evaporated to a syrup, mixed with unreacted solids, and dried to produce an animal feed byproduct.

11 Claims, 1 Drawing Sheet

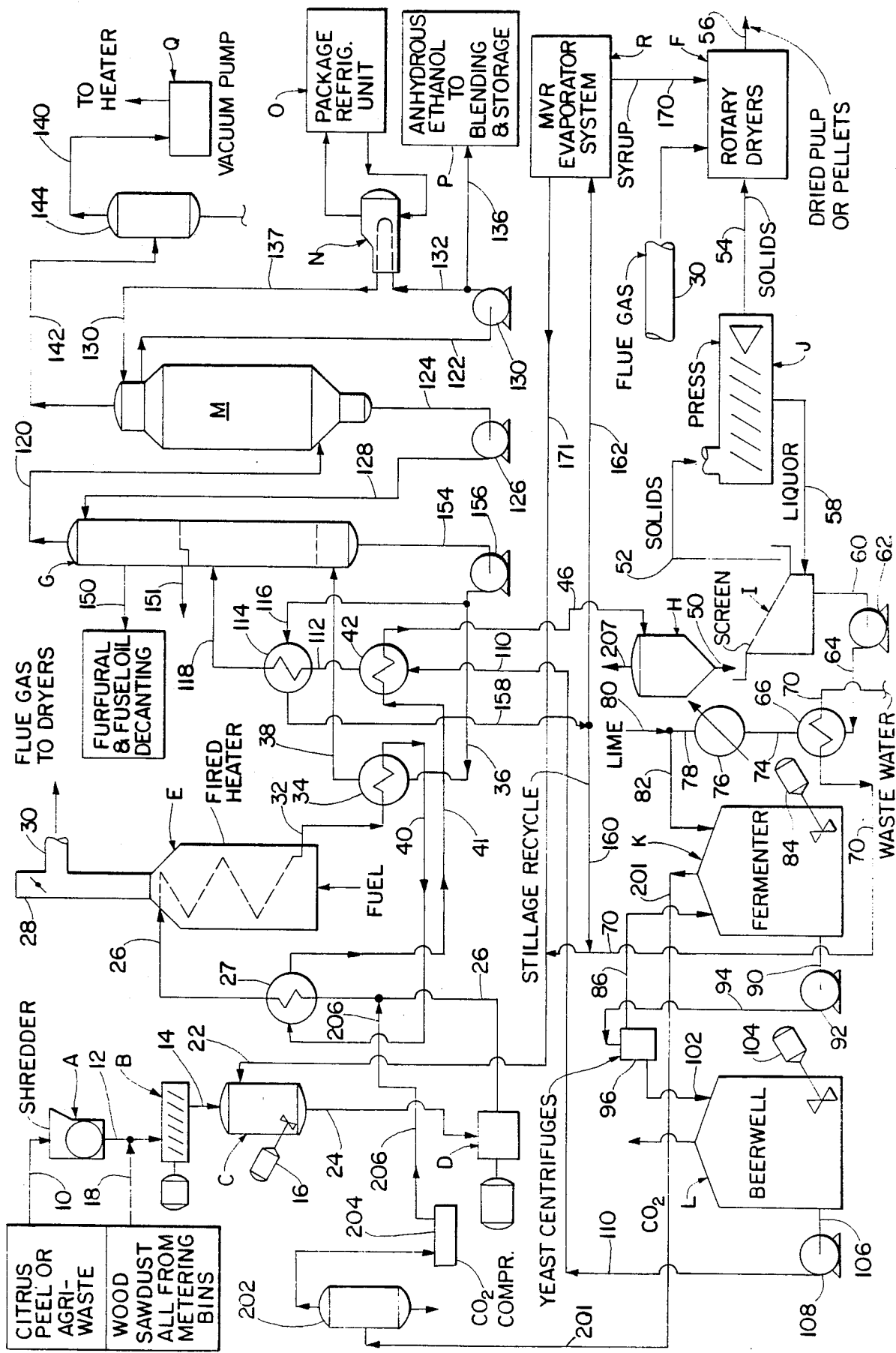

METHOD FOR PRODUCING ETHANOL FROM BIOMASS

BACKGROUND OF THE INVENTION

This application concerns production of ethanol and, more particularly, to conversion of biomass for producing ethanol. The invention is particularly applicable to conversion of wood and agricultural wastes to produce ethanol. However, it will be appreciated that certain aspects of the invention have broader applications.

The Scholler, Madison and Bergius acid hydrolysis processes for the manufacture of ethanol from abundant wood waste have been proposed and/or practiced in the past. However, all are considered uneconomical due mainly to either being highly capital intensive with associated high operating costs, or to the low yields obtained. Recent technology, such as the enzymatic Gulf process and the Stake technology, show substantial improvement in yield, but yet remain capital intensive.

Citrus residue (peel, pulp and seed), another abundant biomass source, is presently processed, in a marginally profitable operation, to produce animal feed and citrus molasses. This operation is necessitated to alleviate a serious disposal problem. In the State of Florida alone, over one million tons of dried citrus pulp and pellets are produced annually which is equivalent to the processing of nearly eight million tons of citrus residue. Additional large tonnages are processed in California, Arizona and Texas.

The citrus peel, including pulp, rag and seed, is presently shredded, and treated with an alkaline slurry or powder, such as lime, intimately contacted in a special mixer, and is then pressed to release a "press liquor," thereby reducing the water content of the peel. This in turn reduces the heat load on the dryers which subsequently produce the dried animal feed. The pressed liquor is evaporated to produce a citrus molasses which is either blended with the peel in the drying operation, or is sold separately for production of other byproducts. Citrus culls are disposed of in a similar manner.

In the present state of the art, the small amount of citrus molasses produced in the above-noted operations is used as feedstock to produce ethanol. None is presently produced from wet peel.

Wood and agricultural wastes, such as citrus peel, are in abundance and, therefore, appear to be the best and cheapest feedstocks for ethanol production, providing that an economical process for obtaining a high yield can be found. Cheaper ethanol can then replace the lead phased out of the gasoline pool as the octane booster. Citrus peel can replace citrus molasses as a feedstock for manufacture of beverage or anhydrous ethanol, and provide a substantially higher yield, on a per ton of peel basis.

SUMMARY OF THE INVENTION

It is known that acids, such as sulfurous and carbonic, can be used in the hydrolysis reaction, with little or no neutralization required prior to fermentation of the sugars to ethanol.

In accordance with one aspect of the present application, carbonic acid obtained from the carbon dioxide produced during fermentation is used as the hydrolyzing catalyst.

In accordance with another aspect of the application, certain agricultural wastes, such as citrus peel and cull fruit, are self-sufficient in organic acid to effect hydrolysis without addition of another acid. Under these special cases, the organic acid acts as the hydrolysis catalyst, and carbon dioxide need not be added. Chemical costs in this acid hydrolysis scheme are thus practically eliminated.

Citrus peel contains a substantial amount of sugar and other solids, such as pectinous substances, hemicellulose and amorphous cellulose. These other solids can be hydrolyzed into additional C6 sugars by utilizing the citric acid present in the peel as the hydrolysis catalyst. In existing operations for processing citrus peel, all of the carbohydrate is diverted to production of animal feed and citrus molasses. The present invention will increase the fermentable sugar content of the peel, which in turn will produce ethyl alcohol from the fermentable sugars, and only the small amount of unconverted solids remaining after hydrolysis will be evaporated and dried for production of animal feed.

For conversion of citrus peel to produce ethanol, the present invention is very economical, because it can be retrofitted into an existing citrus processing plant, or to an existing distillery producing ethanol from citrus molasses, where some of the existing equipment (most major equipment in the case of the distillery), support staff, and facilities can be employed. In such existing plants, the peel is considered a waste material, and is used as the feedstock in the apparatus and method of the present application. The present invention is simple, because only water is mixed with shredded peel. No acid is required for the hydrolysis reaction, because the organic citric acid in the peel is sufficient to carry out the hydrolysis reaction of the convertible biomass to sugars. Feedstock is not limited to peel alone. Citrus culls and other agricultural wastes containing sufficient organic acid can also be used.

Citrus wastes are processed in the apparatus and method of the present application by shredding citrus peel, mixing with water in an agitating vessel, and then pumping, preferably by a triplex or rotary gear pump, to an externally heated hydrolyzer which is a short residence time oil or gas fired heater (furnace). The effluent mash from the heater exchanges heat to a distillation tower reboiler; then to a feed-to-effluent heat exchanger; then to a distillation tower feed heat exchanger; and is finally depressured in a vessel which feeds a liquid/solid separator, such as an inclined or vibrating screen, where wort is separated from the undissolved solids. The solids are then pressed to remove additional water, and then routed to rotary dryers. A rotary filter or centrifuge may be used in lieu of the screen and press. The pressed liquid is pumped with the wort to cooling exchanger(s), and then routed to a continuous fermentation system. Before entering the fermentation system, some neutralization is required to increase the liquor pH. Yeast is added for fermentation only at startup. During operation, the yeast is centrifuged from the beer and is recycled. Essential oils in the peel (d-limonene and terpenes) do not inhibit fermentation since the wort is highly diluted, and a substantial portion of the oil can be recovered as overhead during flashing after depressurizing.

The fermented liquor (beer) is pumped to the furnace effluent-feed heat exchanger, a tower bottom to feed heat exchanger, and is fed to a distillation tower operating at essentially atmospheric pressure. Tower bottoms, commonly known as thin stillage, which is essentially water with dissolved and some undissolved solids, are partially vaporized in the reboiler, and the remaining further preheats the atmospheric tower feed and is pumped to a MVR (mechanical vapor recompression) evaporator system, where a syrup is produced to blend with unconverted peel in the rotary dryers. Some of the stillage is recycled for mash preparation. The overhead from this distillation tower is taken as a vapor to feed a vacuum distillation tower where anhydrous ethyl alcohol is produced as overhead product and the bottoms provide reflux to the first tower.

The fermentation, evaporation and drying systems are considered state of the art operations. However, the hydrolysis and distillation systems as proposed by this present invention have heretofore not been considered in the alcohol industry.

A grass roots facility can be built employing the present invention. For example, many of the citrus processing plants in Florida are centrally located, so that peel could be delivered to the facility at minimum cost. However, if the invention is retrofitted to an existing citrus processing plant, or to a distilling plant presently producing ethanol from citrus molasses, there are many advantages to be gained. Some existing equipment, such as shredders, conveying equipment, presses, screens, rotary dryers, evaporators, and support facilities and staff, are already in place. In a distilling plant, most of the major equipment is already in place. Some of the waste water can be used as makeup water for mash preparation, thereby reducing the load on the existing waste water treatment facility.

The present invention is also advantageous to a citrus processor, in that the dried citrus animal feed will contain more protein due to the yeast produced. A high protein feed is more desirable for cattle.

One disadvantage to this process is that the citrus industry is seasonal. Operation for production of ethyl alcohol could be extended, at the most, to eight or nine months of the year. To provide continuous operation throughout the year, will require a substitute feed for about three or four months. Some feedstocks which can be used are grain, sugar, molasses or biomass such as wood sawdust.

In the case of wood, shredded agricultural biomass, and other biomass feedstocks, lacking in organic acid, carbonic acid must be used as the hydrolyzing catalyst. The biomass is mixed with water in an agitating vessel, and the slurry is then pumped to the fuel fired hydrolyzer. Carton dioxide generated in the fermenter is compressed to the pump discharge pressure, and mixed with the slurry before entering the fired heater hydrolyzer.

It is a principal object of the present invention to provide an improved apparatus and method for conversion of biomass to produce ethanol.

It is another object of the present invention to provide such an apparatus and method which are economical and simple.

It is also an object of the invention to provide such an apparatus and method which do not require the use of supplemental acid as a hydrolyzation catalyst.

It is a further object of the invention to provide such an apparatus and method having improved hydrolyzing and distillation arrangements.

BRIEF DESCRIPTION OF THE DRAWING

The drawing is a schematic flow chart showing apparatus constructed in accordance with the present application for carrying out the method of the present application, and with flow directions indicated by arrows.

DESCRIPTION OF PREFERRED EMBODIMENTS

Referring now to the drawing, wherein the showings are for purposes of illustrating certain preferred embodiments of the invention only, and not for purposes of limiting same, biomass such as citrus peel or agricultural waste flows along path 10 to a shredder means A for shredding the waste. The shredded biomass flows along path 12 to a conveyor B for discharge along flow path 14 to agitating means C in the form of an agitating vessel having an agitator 16.

Instead of using citrus peel or agricultural waste, wood sawdust or the like can be fed along flow path 18 to the flow path 12 downstream of the shredder means A. Wood waste received as chips and sawdust is first screened. The oversized chips are conveyed to an attrition mill and recycled, after milling, so that feed to the mixing vessel is of sawdust consistency, or about 20 mesh and smaller particles.

The biomass in the agitating means C is mixed with water as indicated by a water flow path 22. Where the biomass is citrus peel, about one-fourth to one-third of a gallon of water is added for each pound of peel. When the biomass is wood sawdust, it is mixed with water in a ratio of about 8–10 parts water to one part oven dried wood waste, by weight. The temperature of the biomass slurry in the agitating means C is maintained at about 140°–190° F.

The biomass slurry flows along path 24 from the agitating means C to pump means D which is preferably a triplex or rotary gear pump. However, other pumps, including single screw pumps, can be used. The pump is preferably powered through a variable speed drive so that the discharge rate can be selectively varied. Biomass slurry moves along path 26 from the pump means D to an effluent-to-feed heat exchanger 27, where the slurry is preheated prior to entering hydrolysis means E in the form of a fuel fired heater. The heater may be fired by oil, gas, or a coal or lignin fired fluid bed combustion unit.

When the biomass is citrus waste, the citric acid present in the biomass itself acts as the hydrolyzation catalyst. With citrus waste biomass, the hydrolysis reaction time from inlet to exit of hydrolysis means E should be limited to not more than about three minutes, and preferably to less than about two minutes, in order to suppress destruction of sugars. Heat flux in the radiant section of the heater should be about 10,000–12,000 BTU/hr/sq. ft., and the mash velocity should preferably be maintained at about 3–6 ft./sec., to minimize carmelization or destruction of the sugars.

Efficiency of the heater design for the hydrolysis means E should be such that sufficient heat is made available for the subsequent solids drying operation by using heater flue gas. Heater tube side outlet pressure should be maintained high enough to suppress vaporization. The preferred operation is to maintain the outlet temperature of the hydrolysis means E as high as possible, compatible with the heat requirements for the atmospheric distillation tower. A typical range for outlet conditions when using citrus peel is about 67–415 psia and about 300°–450° F.

When using wood or other biomass that does not contain sufficient organic acid to act as the hydrolyzation catalyst, carbonic acid produced within the system is used as the hydrolyzing catalyst. Carbon dioxide obtained from the fermenter is compressed to pump discharge pressure, and mixed with the biomass slurry before entering the hydrolysis means E. Effluent from the heated hydrolysis means E is maintained at about 400–500° F., and at a pressure from about 365–515 psia, preferably a minimum of about 365 psia, in order to keep sufficient carbon dioxide in solution as carbonic acid to carry out the hydrolysis of hemicellulose and cellulose to glucose.

An advantage of using a fuel fired heater as the hydrolysis means, and carbonic acid as the hydrolyzation catalyst, is that as temperature rises in the heater, carbon dioxide is released from solution so that at the high outlet temperature, the effluent is in contact with acid for a very short time. For example, residence time of the biomass slurry in the heater can be in the order of about five minutes, but exposure to carbonic acid at say an outlet temperature of about 450° F. is much less than about one minute. When operating at about 400–700 psia and about 140–300° F. at the hydrolysis means inlet, sufficient carbonic acid is held in solution to catalyze the hydrolysis reaction even as temperature is rising in the hydrolysis means.

Some destruction of wood sugars is inevitable, but at the high temperatures of 400–500° F., the hydrolysis rate is much faster than that of the sugar decomposition rate. In addition, because stillage recycling is employed, the C5 sugars are returned to the conversion heater, and are decomposed at a faster rate than the C6 sugars.

When using hydrolysis conditions for wood or other non-citric biomass, the remaining lignin and unreacted cellulose, after conversion of hemicellulose and cellulose, can be blended with syrup from an evaporation step, to produce a dried high protein cattle feed as a substitute for hay. Other lignin disposal schemes as practiced in the pulping industry can also be employed.

The heater hydrolysis means E is preferably operated at a temperature such that the temperature of the biomass therein is raised to a temperature of about 400–500° F. for wood waste, and about 300–450° F. for citrus waste, in not more than about 2–5 minutes. The residence time of the biomass in the hydrolysis means E, between entrance and discharge, is about 2–5 minutes. In this manner, the biomass is exposed to the high discharge temperature for a very short time.

The fuel fired heater defining the hydrolysis means E has a flue gas exhaust 28 and a flue gas diversion conduit 30 connected to rotary dryers indicated at F in the lower right of the drawing.

Effluent mash from the hydrolysis means E moves along path 32 to a reboiler 34 wherein heat from the effluent mash is transferred to liquid flowing through a stillage recirculation line 36. A vapor-liquid stream 38 is returned to the bottom section of an atmospheric distillation tower G.

Effluent mash flows from the heat exchanger 34 along a flow path 40 to the heat exchanger 27 wherein heat from the effluent mash is transferred to the biomass slurry being fed into hydrolysis means E. The effluent mash then travels from the heat exchanger 27 along path 41 to heat exchanger 42 wherein heat from the effluent mash is transferred to fermented feed liquor (beer) being supplied to the distillation tower G. Effluent mash from the heat exchanger 42 flows along path 46 to a depressurization vessel H wherein the effluent mash is depressurized.

The effluent mash is discharged as indicated at 50 from depressurizing means H, and is fed to a liquid/solid separator means I that may be in the form of an inclined or vibrating screen. The solids travel along path 52 from liquid/solid separator means I to press means J where the solids are pressed to remove further liquid therefrom. The solids from press means J move along path 54 to rotary dryers F and are finally discharged as indicated at 56 in the form of dried pulp or pellets.

The liquor from press means J travels along path 58 for mixture with the wort discharged from liquid/solid separator means I as indicated at 60. The mixed liquor is transferred by a pump 62 along a path 64 to a heat exchanger 66 where heat is transferred from the liquor to a makeup water line 70 that is connected with line 22 leading to agitating means C. Makeup water line 70 may carry waste water from an existing citrus waste processing plant. The liquor flows from heat exchanger 66 along a path 74 to another heat exchanger 76 through which cooling water flows for removing further heat from the liquor.

It is desirable to at least partially neutralize the liquor before fermentation in order to increase its pH, and the liquor discharged from heat exchanger 76, as indicated at 78, is mixed with lime or another suitable alkaline substance as indicated at 80. The mixed liquor is then fed along path 82 to fermenting means K that includes a mixer 84. Yeast is added to fermenting means K only for startup of the fermentation process.

The fermented liquor (beer) from fermenting means K is discharged as indicated at 90 to a pump 92 which feeds the beer along path 94 to a yeast centrifuge 96 for removing sufficient yeast from the beer, and recycling same through line 86 to maintain a high yeast population in fermenting means K. The beer then flows along path 102 to beer well means L having a mixer 104. Essential oils in the peel do not inhibit the fermentation process, because the wort is highly diluted, and a substantial portion of the oil is flashed with the overhead in depressurization means H.

The beer is discharged from beer well means L as indicated at 106, and is transferred by pump 108 along path 110 to heat exchanger 42 for receiving heat from the effluent mash flowing through the heat exchanger 42 from the hydrolysis means E. The beer then flows along path 112 to another heat exchanger 114 wherein the beer receives further heat from stillage flowing through line 116 from the bottom section of distillation means G. The beer then travels along path 118 as feed to distillation tower means G.

The distillation tower means G operates at essentially atmospheric pressure, and the overhead therefrom is discharged along path 120 as a vapor to feed vacuum tower distillation means M where anhydrous ethyl alcohol is produced as an overhead product and discharged therefrom as indicated at 122. The bottoms from vacuum distillation tower means M are discharged as indicated at 124 and fed by pump 126 along path 128 back to distillation tower means G to provide reflux therefor.

The ethyl alcohol vapor at about 190 proof is transferred along path 120 from the distillation tower means G to the flash zone of the packed distillation vacuum tower means M, and moves through a suitable control valve which maintains the atmospheric tower top pressure by means of pressure control.

An overhead liquid sidestream draw from packed vacuum distillation tower means M travels along path 122 to a pump 130 which feeds the effluent along a path 132 through refrigerant evaporator means N where the draw stream is cooled by heat exchanged to vaporizing refrigerant as the coolant.

A package refrigeration unit connected with cooling means N is indicated at 0. Anhydrous ethyl alcohol product is withdrawn from line 132 as indicated at 136 to a blending and storage means P. The alcohol that is not withdrawn through line 136 is fed along path 137 back to the top of the packed vacuum distillation tower means M as indicated at 138 to serve as reflux and direct contact condensing medium.

A dry vacuum pump Q is connected by line 140 and 142 to the top of tower M through knock-out drum means 144 for removing condensables. Discharge from the vacuum pump Q may be routed to a special burner associated with the hydrolysis means E to serve as auxiliary fuel.

Fusel oil and/or furfural recovered from the atmospheric tower means G can be decanted as indicated at 150 for use as fuel for the hydrolysis means E, or it can be blended back into the alcohol if it is destined for gasohol production. When fruit waste is being processed, the essential oils can be recovered and decanted in a similar manner as the fusel oil, at a location 151 below the fusel oil decanting line 150.

The packed vacuum distillation tower means M operates at a vacuum well below that pressure at which the azeotrope disappears. The vacuum tower may operate at a top pressure of about 20–40 mm Hg, and a bottom pressure of about 30–55 mm Hg. Most preferably, typical operating pressure is about 30 millimeters of mercury at the top, and about 40–45 millimeters mercury at the flash zone. An adequate height of packing is provided for distillation, along with sufficient heat transfer packing at the tower top, required to condense the reflux and side stream draw.

Atmospheric tower bottoms, commonly known as thin stillage, which is essentially water with dissolved and some undissolved solids, are partially vaporized, and the remaining further preheats the feed and is pumped to a mechanical vapor recompression evaporator system R. Stillage from the distillation tower means G is discharged from the bottom thereof as indicated at 154, and is fed by pump 156 to heat exchangers 34 and 114. The stillage flowing through reboiler 34 is directed back into the bottom section of tower G through line 38.

The stillage flowing through heat exchanger 114 travels along path 158 to flow paths 160 and 162. Part of the stillage flows along path 160 to make up water line 70 which connects to line 22 for feeding the agitating means C. The remainder of the stillage flows along path 162 to a mechanical vapor recompression evaporator means R (MVR) where a syrup is produced and discharged as indicated at 170 for blending with unconverted citrus peel or other biomass in the rotary dryers F. Condensate from the MVR is recirculated as indicated at 171 to line 22 feeding liquid to the agitating means C.

When wood or other biomass lacking in organic acid is used as the feedstock, carbon dioxide generated in the fermenting means K is withdrawn therefrom as indicated at 201, and flows to a knock-out drum 202 and a compressor 204. The carbon dioxide is compressed to a pressure greater than the discharge pressure of the pump D for the effluent mash from the agitating means C. The compressed carbon dioxide is then fed through line 206 to effluent mash line 26 where it dissolves in the solution to form carbonic acid that acts as the hydrolysis catalyst in the hydrolysis means E.

Decanting and recovery facilities for essential oils from citrus peel and/or furfural from wood wastes which flash at depressurizing means H are not shown. Line 207 is directed to those facilities from depressurizing means H. A substantial portion of either essential oils or furfural can be recovered from the flashed overhead. The operation at depressurizing means H can be at about 240–275° F. inlet and flashing to atmospheric conditions.

It will be recognized that liquid/solid separator means I and press J could be replaced with a rotary filter or centrifuge if so desired. The arrangement shown and described separates the undissolved solids prior to fermentation, and this results in the loss of a small amount of sugar with the solids, which is thus not available for fermentation to ethyl alcohol. In the alternative, it is possible to route all of the mash to fermentation and distillation. In the interest of minimizing fouling in the heat exchangers, yeast centrifuges and the atmospheric distillation tower means, the arrangement shown and described is preferred even though a small amount of sugar is sacrificed.

The improved distillation arrangement of the present application avoids the use of chemical contaminants or solvents such as benzene to produce anhydrous ethanol. This is particularly advantageous in a facility that handles products for human consumption. Distillation systems other than those shown and described may be employed with the hydrolysis system of the present application. Where the capacity of the plant is small, mol sieve dehydration can be used.

If it is desirous to produce about 190 proof beverage or industrial alcohol, then the vacuum column and its associated equipment will not be required. Such is the case when this invention is retrofitted to an existing distillery presently utilizing citrus molasses as feedstock. The necessary distillation equipment is state-of-the-art at any distillery producing 190 proof ethanol.

Where corn is the feedstock, it is possible to feed kernels which are either whole or just cracked in order to save milling horsepower. The kernels fed to the hydrolysis means E include, along with the starch, about 30% fiber which is mostly hemicellulose. Some of this fiber can be converted to fermentable sugars via carbonic acid hydrolysis thereby increasing alcohol yield.

In the present application, heat recovery is shown in simplest form, and can be optimized for a specific operation. The scheme is conducive to recovery of heat in a convection section of the fired heater to serve other useful purposes, such as for generating steam or for air preheating. Co-generation is also a distinct possibility.

Although the invention has been shown and described with respect to certain preferred embodiments, it is obvious that equivalent alterations and modifications will occur to others skilled in the art upon the reading and understanding of this specification. The present application includes all such equivalent alterations and modifications, and is limited only by the scope of the claims.

I claim:

1. A method of producing ethanol from biomass comprising the steps of providing biomass containing organic acid, mixing said biomass with water to form a biomass slurry, hydrolyzing said slurry in fuel fired hydrolysis means, utilizing said organic acid for catalyzing hydrolysis of said slurry, separating said slurry into liquid and solids after said hydrolyzing step, utilizing flue gas from said fuel fired hydrolysis means for drying said solids, and further processing said liquid to produce ethanol.

2. A method of producing ethanol from biomass comprising the steps of providing biomass containing organic acid, mixing said biomass with water to form a biomass slurry, hydrolyzing said slurry at a temperature and pressure for catalyzing hydrolysis of said slurry with said organic acid that is contained in said biomass, and further processing effluent from said step of hydrolyzing to produce ethanol.

3. The method of claim 2 including the step of fermenting at least part of the effluent from said hydrolyzing step to generate carbon dioxide, selectively utilizing at least part of said carbon dioxide in the form of carbonic acid for supplementing catalysis of said slurry during said hydrolyzing step, and said step of further processing effluent to produce ethanol being carried out subsequent to said fermenting step on effluent sued for said fermenting step.

4. A method of producing ethanol from biomass comprising the steps of providing biomass containing organic acid that is naturally present in the biomass, mixing said biomass with water to form a biomass slurry, hydrolyzing said slurry at a temperature and pressure for catalyzing hydrolysis of said slurry with said organic acid that is naturally present in the biomass without the addition of any additional acid, and further processing effluent from said step of hydrolyzing to produce ethanol.

5. The method of claim 4 wherein said step of providing biomass is carried out by providing biomass that is primarily citrus residue.

6. The method of claim 4 wherein said hydrolyzing step is carried out by hydrolyzing said slurry in fuel fired hydrolysis means.

7. The method of claim 6 including the step of operating said hydrolysis means at a temperature for raising the temperature of said slurry to about 300–400° F. in about 2–5 minutes.

8. The method of claim 4 wherein said slurry is hydrolyzed at a pressure sufficient to suppress vaporization of said slurry.

9. The method of claim 8 wherein said pressure is about 67–415 psia.

10. The method of claim 4 wherein said step of further processing effluent from said step of hydrolyzing includes the steps of distilling effluent from said hydrolyzing step to form ethyl alcohol vapor, and feeding said vapor to packed vacuum distillation tower means for producing anhydrous ethyl alcohol.

11. The method of claim 4 wherein said biomass consists essentially of citrus peel.

* * * * *